United States Patent [19]

Stokker

[11] Patent Number: 4,588,820

[45] Date of Patent: May 13, 1986

[54] PROCESS FOR EPIMERIZATION AT $C_6$ OF 3,4,5,6-TETRAHYDRO-2H-PYRAN-2-ONE

[75] Inventor: Gerald E. Stokker, Gwynedd Valley, Pa.

[73] Assignee: Merck & Co., Inc., Rahway, N.J.

[21] Appl. No.: 619,506

[22] Filed: Jun. 11, 1984

[51] Int. Cl.$^4$ .......................................... C07D 309/10
[52] U.S. Cl. .................................. 549/292; 549/214; 556/419; 556/420
[58] Field of Search ................ 549/214, 292

[56] References Cited

U.S. PATENT DOCUMENTS 4,198,425 4/1980 Mistui et al. ...................... 549/292
4,444,784 4/1984 Hoffman et al. .................. 549/292

FOREIGN PATENT DOCUMENTS 0068038 1/1983 European Pat. Off. ............ 549/292

OTHER PUBLICATIONS

March, Jerry, Advanced Organic Chemistry: Reactions, Mechanisms & Structure, McGraw-Hill, N.Y. (1968) pp. 268–269, 372–375.

Eliel, Ernest, Stereo Chemistry of Carbon Compounds, (1962) McGraw-Hill Book Co., N.Y., pp. 116–119, 38–39.

Johnson et al, Nucleophilic Displacement on Sulfur, The Inversion of Sulfoxide Configurations, Journal Amer. Chem. Society, vol. 87, No. 23, pp. 5404–5409 (1965).

Primary Examiner—Glennon H. Hollrah
Assistant Examiner—D. L. Dinner
Attorney, Agent, or Firm—Joseph F. DiPrima; William H. Nicholson; Michael C. Sudol

[57] ABSTRACT

An external bond at the 6-position of a 3,4,5,6-tetrahydro-2H-pyran-2-one, as found in the 3-hydroxy-3-methylglutaryl-coenzyme A reductase inhibitors, is readily epimerized by treating an amide of the corresponding hydroxy acid with a sulfonyl chloride reagent.

3 Claims, No Drawings

PROCESS FOR EPIMERIZATION AT C₆ OF 3,4,5,6-TETRAHYDRO-2H-PYRAN-2-ONE

SUMMARY OF THE INVENTION

This invention is concerned with a novel process whereby an external bond at the 6-position of a 3,4,5,6-tetrahydro-2H-pyran-2-one, as found in the 3-hydroxy-3-methylglutaryl-coenzyme A reductase inhibitors, is readily epimerized by treating an amide of the corresponding hydroxy acid with a sulfonyl chloride reagent. By this means a biologically inactive cis-isomer is transformed into an active antihypercholesterolemic trans-isomer useful in the treatment of hyperlipemia, familial hypercholesterolemia and atherosclerosis.

BACKGROUND OF THE INVENTION

Endo et al., *J. Antibiotics*, XXIX, 1346 (1976) described a fermentation product, ML-236B, with potent antihypercholesterolemic activity which acts by inhibiting HMG-CoA reductase. This material, named compactin by Brown et al., *J. Chem. Soc., Perkin I*, 1165 (1976) was shown to have a desmethyl mevalonolactone partial structure and the stereochemistry was studied.

Shortly thereafter a chemically similar, natural product MK-803 (mevinolin), obtained by fermentation, was isolated and characterized, by Monaghan et al., U.S. Pat. No. 4,231,938. It has been shown to have the same desmethyl mevalonolactone partial structure and the absolute stereochemical configuration has been determined and described in EPO publication No. 0,022,478 of Merck & Co., Inc.

Totally synthetic analogs of these natural inhibitors have been prepared and described in Sankyo's U.S. Pat. No. 4,198,425 and Sankyo's U.S. Pat. No. 4,255,444 with no attempt being made to separate the stereo- and optical isomers. Subsequently, as described in Merck's EPO publication No. 0,024,348 and by Meyer, *Ann. Chem.*, (1979), pages 484–491, similar totally synthetic analogs were separated into their stereoisomers and optical enantiomers. Furthermore, it was shown in EPO publication No. 0,024,348 that essentially all of the HMG-CoA reductase activity resides in the 4(R)-trans species as is the case with the naturally occurring compounds compactin and mevinolin.

In the prior art process for preparing the totally synthetic compounds, the lactone moiety of each compound had to be elaborated by a lengthy series of synthetic operations followed by very tedious and expensive chromatographic separation of the cis, trans racemates, or enantiomers, following which, the inactive cis-isomer would be discarded.

Now, with the present invention the inactive cis-racemate or enantiomer can be epimerized to the biologically active trans-isomer.

DETAILED DESCRIPTION OF THE INVENTION

The novel process of this invention can be depicted as follows:

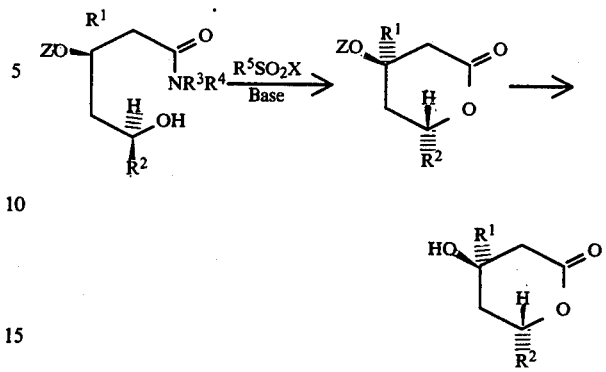

wherein:

X is halo such as chloro, bromo or iodo, especially chloro;

2 is a carbinol protecting group such as
 (a) trialkylsilyl especially tert-butyldimethysilyl, or
 (b) carboxyacyl especially acetyl;

$R^1$ is
 (a) hydrogen, or
 (b) methyl;

$R^3$ and $R^4$ are independently
 (a) hydrogen,
 (b) $C_{1-3}$ alkyl, or
 (c) phenyl-$C_{1-3}$ alkyl, wherein the phenyl is unsubstituted or substituted with
   (i) $C_{1-3}$ alkyl,
   (ii) $C_{1-3}$ alkoxy or
   (iii) halo, such as fluoro, chloro or bromo;

$R^2$ is
 (a)

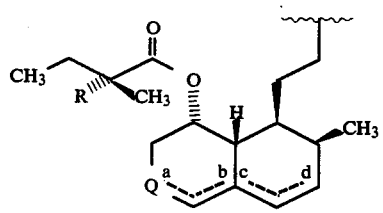

wherein Q is

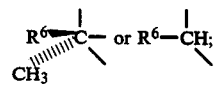

$R^6$ is H or OH;

R is hydrogen or methyl, and a, b, c, and d represent optional double bonds, especially wherein b and d represent double bonds or a, b, c, and d are all single bonds; or (b)

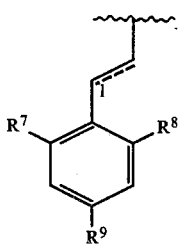

wherein R[7] is phenyl or benzyloxy in which the phenyl in each case can be substituted with one or more substituents selected from $C_{1-3}$ alkyl, and halo such as fluoro, chloro or bromo, and R[8] and R[9] are $C_{1-3}$ alkyl or halo, and e represents an optional double bond, especially wherein R[2] is:

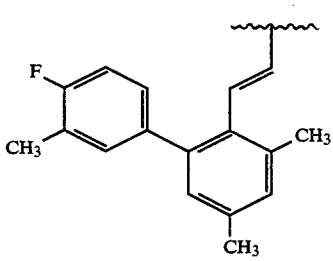

and
R[5] is (a) $C_{1-3}$ alkyl, especially methyl, or
(b) phenyl, either unsubstituted or substituted with one or two $C_{1-3}$ alkyl groups, especially phenyl or toluyl.

The novel process comprises treating an amide, as shown as starting material in the reaction scheme with an organic sulfonyl halide, especially methanesulfonyl chloride under reaction conditions that would favor O-sulfonylation of the 5-carbinol. For example the amide and the sulfonyl halide are combined in an inert organic solvent such as a chlorinated hydrocarbon such as methylene chloride, chloroform, 1,2- or 1,1-dichloroethane, or an ether such as THF, diethyl ether or 1,2-dimethoxyethane, or the like at $-10°$ C. to about $+10°$ C. with stirring, and the mixture is allowed to warm spontaneously to room temperature over about 2 to about 8 hours, preferably about 4 hours. From 1 to 2 molar equivalents of sufonyl halide is used per mole of amide, and preferably from 1 to about 1.2 molar equivalents. It is also preferable to employ an acid acceptor in the reaction mixture such as a tertiary amine such as triethyl amine, pyridine or the like, an inorganic base such as an alkali metal carbonate or bicarbonate, or a basic ion exchange resin, and preferably in an amount sufficient to trap the hydrogen chloride liberated during the reaction, usually a slight excess relative to the amount of sulfonyl halide used.

Removal of the 4-hydroxy protecting group is carried out by standard procedures known in the art. For example, the silyl group is removed by treatment with three equivalents of tetrabutylammonium flouride and four equivalents of acetic acid per equivalent of silyl compound in an ethereal solvent such as THF, ether, 1,2-dimethoxyethane or the like at about 10° C. to 25° C., preferably at room temperature for about 4 to 15 hours.

The starting amides are prepared from the 4-hydroxy-3,4,5,6-tetrahydra-2H-pyan-2-ones by first protecting the 4-hydroxy group by silyation, or acylation as described in U.S. Pat. No. 4,444,784 (silylation) and U.S. Pat. No. 4,198,425 (acetylation) followed by treatment of the lactone with an excess of a primary or secondary amine in a chlorinated hydrocarbon as previously defined with warming, usually to the reflux temperature for about 20 to 24 hours. The reaction is best mediated with trimethyl aluminum as described by Weinreb et al., in *Tetrahedron Letters,* (1977), 4171, especially with secondary amines.

EXAMPLE 1

The 6(R) - Epimer of Mevinolin

Step A: Preparation of N-Benzyl 3-O-dimethyltert-butylsilylmevinolinamide

Trimethyl aluminum (495μL of 2.43 M in hexane, 1.2 mmol) was added slowly at room temperature to a solution of 128 mg benzylamine (131 μL, 1.2 mmol) in 3 mL of methylene chloride under argon. The mixture was stirred at room temperature for 15 minutes and 518 mg of 4-O-dimethyl-tert-butylsilyl-mevinolin in 3 mL of methylene chloride was added. The solution was stirred at 40° C.–45° C. for 20 hours. The cooled reaction mixture was distributed between 100 mL of ether and 100 mL of cold 1N hydrochloric acid. The layers were separated and the ether layer was washed with 2×100 mL of water, dried and evaporated to dryness to yield 500 mg. as a pale amber gum.

Step B: 4-O-Dimethyl-tert-butylsilyl -6(s)-epi-Mevinolin

A mixture of 500 mg (0.8 mmol) of the amide from Step A, 15 mL of methylene chloride, 200 μL (1.4 mmol) of triethylamine, and 78 μL (1.0 mmol) of methanesulfonyl chloride was stirred at 0° C. under nitrogen and while stirring was allowed to warm spontaneously to 20° C. The crude product (480 mg) was isolated as described in Step A and then purified by low pressure chromatography on a 150×50 mm. column of silica by elution with 20:1 (v:v) $CH_2Cl_2$: $CH_3OH$ to provide 53 mg of pure product.

Step C: Preparation of the 6(R)-epimer of Mevinolin

The product from Step B (50 mg) was dissolved in 1 mL of THF and treated with 280 μL (280 mmol) of tetrabutylammonium fluoride and 22 μL (380 mmol) of acetic acid. The mixture was stirred 7 hours at room temperature, diluted with 150 mL of ether, washed with 10 mL of 1N hydrochloric acid and 2×20 mL of saturated sodium bicarbonate, dried and evaporated to dryness. The residue was chromatographed on a 150×30 mm low pressure column of silica by elution with 9:1 (v:v) $CH_2Cl_2$:$CH_3OH$ to give 17 mg of product, as a clear colorless glass.

Employing the procedures substantially as described in Example 1, Steps A through C but substituting for the 4-O-dimethyl-tert-butylsilylmevinolin used in Step A, an approximately equimolecular amount of the starting materials described in Table I there are produced the corresponding epimers also described in Table I.

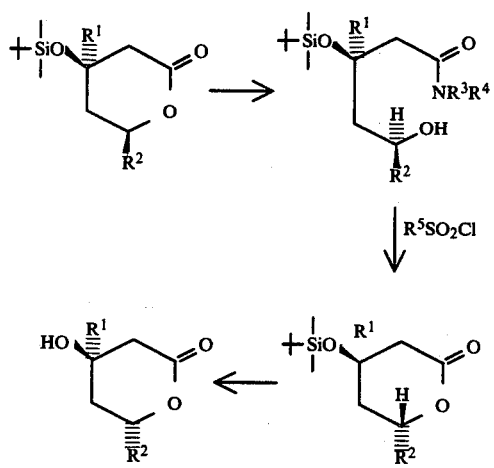

TABLE I

| R² | R¹ | R³ | R⁴ | R⁵ |
|---|---|---|---|---|
| ![F-phenyl-dimethylphenyl vinyl] | H | H | —CH₂C₆H₅ | CH₃— |
| ![methylphenyl with CH3 groups] | H | —CH₃ | —CH₃ | CH₃— |
| ![decalin ester structure] | H | H | —CH₂C₆H₅ | C₆H₅— |
| ![decalin ester structure] | H | H | —CH₂C₆H₅ | CH₃— |
| ![decalin ester dimethyl] | H | —CH₃ | —CH₃ | CH₃— |
| ![decalin ester] | H | H | —CH₂C₆H₅ | CH₃— |
| ![F-phenyl-dimethylphenyl vinyl] | H | H | —CH₂C₆H₅ | CH₃— |

TABLE I-continued

| R² | R¹ | R³ | R⁴ | R⁵ |
|---|---|---|---|---|
| ![phenyl-OCH2-fluorophenyl] | CH₃ | H | —CH₂C₆H₅ | CH₃— |

What is claimed is:

1. A process for preparing a compound of structural formula:

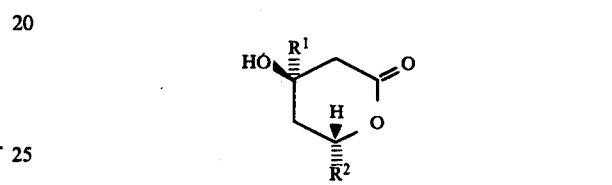

which comprises treating a compound of structural formula:

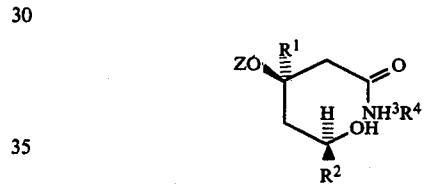

with an organic-sulfonyl halide of structural formula:

R⁵SO₂X wherein:
X is halo;
Z is a carbinol protecting group;
R¹ is
 (a) hydrogen, or
 (b) methyl; R³ and R⁴ are independently
 (a) hydrogen,
 (b) $C_{1-3}$ alkyl, or
 (c) phenyl-$C_{1-3}$ alkyl, wherein the phenyl is unsubstituted or substituted with
  (i) $C_{1-3}$ alkyl,
  (ii) $C_{1-3}$ alkoxy or
  (iii) halo;
R² is
 (a)

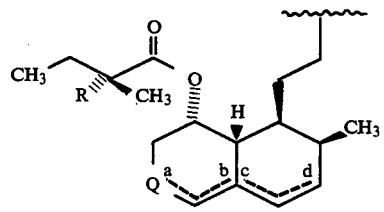

wherein Q is

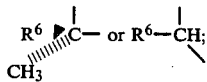

R[6] is H or OH;

R is hydrogen or methyl, and a, b, c, and d represent optional double bonds; or (b)

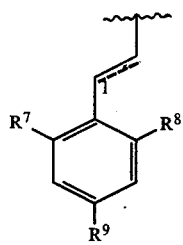

wherein R[7] is phenyl or benzyloxy in which the phenyl in each case can be substituted with one or more substituents selected from $C_{1-3}$ alkyl, and halo, and R[8] and R[9] are $C_{1-3}$ alkyl or halo and e represents an optional double bond;

and R[5] is (a) $C_{1-3}$ alkyl; or (b) phenyl, either unsubstituted or substituted with one or two $C_{1-3}$ alkyl groups.

2. The process of claim 1, wherein X is chloro; Z is trialkylsilyl or carboxyacyl; b and d are double bonds or all of a, b, c and d are single bonds; R[3] is hydrogen and R[4] is benzyl; R[7] is phenyl substituted with $C_{1-3}$ alkyl and fluoro and R[5] is methyl.

3. The process of claim 2 for the preparation of:

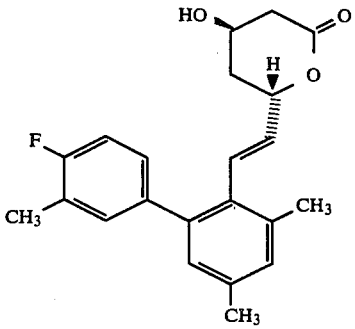

* * * * *

UNITED STATES PATENT AND TRADEMARK OFFICE
CERTIFICATE OF CORRECTION

PATENT NO. : 4,588,820
DATED : May 13, 1986
INVENTOR(S) : Gerald E. Stokker

It is certified that error appears in the above—identified patent and that said Letters Patent is hereby corrected as shown below:

Column 3, in the structure, "1" should be -- e --

Column 7, in the structure, "1" should be -- e --

Signed and Sealed this

Fourteenth Day of October, 1986

[SEAL]

*Attest:*

DONALD J. QUIGG

*Attesting Officer*    *Commissioner of Patents and Trademarks*